United States Patent [19]

Lee

[11] Patent Number: 4,838,275
[45] Date of Patent: Jun. 13, 1989

[54] HOME MEDICAL SURVEILLANCE SYSTEM

[76] Inventor: Arnold St. J. Lee, 1033 Hilts Ave., Los Angeles, Calif. 90024

[21] Appl. No.: 76,998

[22] Filed: Jul. 20, 1987

Related U.S. Application Data

[63] Continuation of Ser. No. 803,123, Nov. 29, 1985, abandoned.

[51] Int. Cl.⁴ ............................................. A61B 5/02
[52] U.S. Cl. .................................. 128/670; 128/904
[58] Field of Search ............... 128/633, 670, 677, 683, 128/687, 694, 714, 904, 906; 221/2, 3, 9, 15; 381/14, 15, 41

[56] References Cited

U.S. PATENT DOCUMENTS

| | | | |
|---|---|---|---|
| 1,078,090 | 11/1913 | Foss | 5/327 R |
| 2,891,111 | 6/1959 | Flanagan | 381/41 |
| 3,106,701 | 10/1963 | Kalfaian | 381/41 |
| 3,302,828 | 2/1967 | Ganez et al. | 221/9 |
| 3,696,805 | 10/1972 | Sweeten et al. | 128/906 |
| 3,726,270 | 4/1973 | Griffis et al. | 128/904 |
| 3,765,406 | 10/1973 | Toole et al. | 128/24 R |
| 3,830,896 | 8/1974 | Flicker et al. | |
| 3,872,251 | 3/1975 | Auerbach et al. | 128/904 |
| 3,963,019 | 6/1976 | Quandt | 128/633 |
| 4,216,462 | 8/1980 | McGrath et al. | 128/904 |
| 4,272,878 | 6/1981 | Danforth | |
| 4,296,756 | 10/1981 | Dunning et al. | 128/904 |
| 4,320,766 | 3/1982 | Alihanka et al. | 128/782 |
| 4,347,213 | 8/1982 | Rogers, Jr. | |
| 4,363,368 | 12/1982 | Paddon et al. | 128/782 |
| 4,412,292 | 10/1983 | Sedam et al. | 221/9 |
| 4,428,381 | 1/1984 | Hepp | 128/904 |
| 4,473,884 | 9/1984 | Behl | 221/3 |
| 4,577,638 | 3/1986 | Graham | 128/671 |
| 4,622,185 | 11/1986 | Kostich | |

FOREIGN PATENT DOCUMENTS

| | | | |
|---|---|---|---|
| 2711556 | 9/1978 | Fed. Rep. of Germany | |
| 487545 | 6/1938 | United Kingdom | 128/677 |

OTHER PUBLICATIONS

"Indirect Heart Rate Measuring Device", Wiberger, 1964, American J. of Medical Elec.
"Light wt. Carbon Fiber Structures...", Manley et al., 1973, Composites.

Primary Examiner—Max Hindenburg
Attorney, Agent, or Firm—Spensley, Horn, Jubas & Lubitz

[57] ABSTRACT

Many subscriber patients are served by this system. In each patient's home is an apparatus that includes special furniture on which the patient lies and sits, and embedded in which are devices that automatically sense multiple parameters related to the patient's health. The patient cooperates only passively. The parameters are so chosen—and are sufficiently numerous and accurate—as to provide in the aggregate a comprehensive profile of the patient's general state of health. The apparatus also generates electronic health-parameter signals related to the sensed parameters, and it transmits these signals from the patient's home to a central surveillance and control office. Equipment there receives the signals, displays corresponding indicia of the parameters, and transmits control signals back to the patient's apparatus. Two-way voice communication between the patient and a highly trained observer at the central office supplements the electronic measurements. The observer conducts routine diagnostic sessions except when an emergency is noted from these sessions or from a patient-initiated communication. The observer determines whether a nonroutine therapeutic response is required, and if so facilitates such a response. Selection among emergency cases follows a highly refined emergency-priority hierarchy.

18 Claims, 3 Drawing Sheets

HOME MEDICAL SURVEILLANCE SYSTEM

This is a continuation of application Ser. No. 0/803,123 filed on Nov. 29, 1985, now abandoned.

1. INTRODUCTION

In view of the considerable length of this document and the complexity of the subject matter, a numbering system and a system of section titles and subtitles have been employed so that those skilled in the art can most readily understand and return to the various parts of this document. Following is a list of the numbered sections of this text that precede the claims.

1. INTRODUCTION
1.1 BACKGROUND
1.1.1 FIELD OF THE INVENTION
1.1.2 PRIOR ART
1.2 BRIEF SUMMARY OF THE DISCLOSURE
1.3 BRIEF DESCRIPTION OF THE DRAWINGS
2. DETAILED DESCRIPTION OF PREFERRED EMBODIMENTS: SYSTEM PHILOSOPHY
2.1 RELIABILITY
2.2 PRIORITIES
2.3 PATIENT INVOLVEMENT
2.4 RECORD KEEPING
2.5 PATIENT/PHYSICIAN RELATIONSHIP
3. DETAILED DESCRIPTION OF PREFERRED EMBODIMENTS: COMPONENTS
3.1 PATIENT SUBSCRIBER APPARATUS
3.1.1 Diagnostic Bed
3.1.2 Diagnostic Chair
3.1.3 Daily Medicine Dispensary
3.1.4 Data Acquisition and Transmission
3.1.5 Communications
3.2 SURVEILLANCE AND CONTROL OFFICE
3.2.1 Data Receipt and Transmission
3.2.2 Other Communication Methods
3.2.3 Records
3.2.4 Data Reduction and Computer Analysis
3.2.5 Data Interpretation by Observer
3.2.6 Observer's Station
3.3 PHYSICIAN'S OFFICE
3.3.1 Data Transmission and Receipt
3.3.2 Acceptance of Call Duty
3.4 EMERGENCY-CALL PHYSICIAN'S OFFICE
3.4.1 Communications
3.4.2 Records
3.5 PARAMEDIC READY ROOM
3.5.1 Communications
3.5.2 Portable Terminal
3.5.3 Instrumentation Diagnostics Kit
3.6 VISITING-NURSE REGISTRY
3.6.1 Communications
3.6.2 Portable Terminal
3.7 PHARMACY
3.8 LAY REFERRAL PERSON
4. DETAILED DESCRIPTION OF PREFERRED EMBODIMENTS: PLAN OF OPERATION
4.1 DIAGNOSTIC DATA ACQUISITION
4.1.1 Routine Diagnostic Session
4.1.2 Emergency Diagnostic Session
4.2 DIAGNOSTIC DATA PROCESSING, EVALUATION, AND RECORDS
4.2.1 Calculation fo Relevant Clinical Values
4.2.2 Display of Relevant Clinical Values and Instrument Traces
4.2.3 Evaluation of Data by Computer
4.2.4 Evaluation of Data by Observer
4.2.5 Storage of Data
4.3 EMERGENCY PRIORITY ALGORITHM
4.3.1 Untoward Vital Signs
4.3.2 Other Untoward Signs
4.3.3 Multiple Untoward Signs
4.4 OBSERVER'S INTERACTION WITH PATIENT
4.4.1 During Routine Surveillance
4.4.2 During Emergency
4.5 PARAMEDICS
4.5.1 Responsibilities During Emergencies
4.5.2 Responsibilities at Other Times
5. DETAILED DESCRIPTION OF PREFERRED EMBODIMENTS: APPENDICES
5.1 GLOSSARY
5.2 ABBREVIATIONS
6. CONCLUSION

1.1 BACKGROUND 1.1.1 Field of Invention

This invention relates generally to the field of providing medical care to ambulatory nonhospitalized patients, and more particularly to a novel system— encompassing both apparatus and method—for monitoring the condition of people whose general physical condition is frail or unstable—but who are still able to live at home.

1.1.2 Prior Art

Historically, people in acute physical distress were visited in their homes by physicians who diagnosed medical problems with the aid of a few simple, crude instruments. With the advent of modern sophisticated diagnostic techniques and equipment, house calls were discontinued.

People in medical distress now must go to the physician's office or to a hospital emergency room for treatment. Adding insult to injury, the patient must often go to another facility such as a specialist's office or a testing laboratory, since the diagnostic equipment in most physicians' offices is insufficient for many diagnoses, especially of cardiovascular malfunctions.

Thus the patient while already ill—and often partly incapacitated—must travel repeatedly and sometimes on short notice to several health-care professionals. Not only does this frequently entail great effort, discomfort and cost, but in addition the stress of these efforts often accelerates the decline of the patient's health, further increasing the cost of medical care.

Furthermore, these circumstances place an unacceptable financial burden on most patients and on the government agencies that underwrite the cost of many patients' health care.

Although many of the patients who are adversely affected by these circumstances are elderly, I wish to emphasize that both the problem area and the population "group" addressed by my invention sweep far more broadly than ministering to the health-services needs of the elderly.

To the contrary, the problems outlined above are of crucial importance to many young and middle-aged people who are part of the general population. These segments of the population are normally expected to be active in wage-earning or family management, but their health problems interfere with those roles. Since they are not at retirement age and often have neither social-security benefits nor savings, these people may from some perspectives be "harder hit" by disabling or semidisabling illness than are the elderly.

Certain prior patents may be worthy of mention in this connection and will be discussed briefly below—particularly U.S. Pat. No. 4,296,756 and certain patents cited in the prosecution of the corresponding patent application.

From these patents it can be seen that adequate technology is at hand for automated remote monitoring of any one of several different health-related parameters considered individually. Further, technology is at hand for automated remote monitoring of certain *closely related groupings* of more than one health-related parameter, where such groupings have been chosen by prior artisans as going to a particular malady of concern.

It can be appreciated from a study of these patents that each of the innovations disclosed in them is potentially a very useful and valuable advance. It can further be appreciated from a review of these patents, however, that they are not addressed to, and do not solve, the problems enumerated above.

The reason is threefold. First, the inventions presented in each of these patents, and also in all of them considered together, are directed to particular relatively narrow areas of medical concern.

Second, most of these inventions involve at least semiactive participation by the patient—stepwise maneuvers or behavior in response to specific instructions from an operator. It will be understood that such a mode of operation places a requirement on the mental organization and sometimes physical capability of the patient, and also places an additional requirement on the time and attentiveness of the operator. This latter point is especially important when there is no operator or aide at the patient's location.

Third, the inventions presented in each of these patents are disclosed almost exclusively to diagnosis, tacitly assuming that proper follow-up measures somehow will be provided outside the scope of the invention itself, and on an ad hoc basis—and these inventions thus lack a component of systematic response to diagnosis that is crucially important.

Therefore as will be seen, these patents fail to address the broad social and technological problem introduced above. This problem arises from the unavailability of house calls to the enormous general population of people who live at home and who are either sick or prospectively sick.

Their sicknesses or prospective sicknesses do not fall into any single convenient category, or even into any specific grouping of categories by relevant parameter. They require not only regular systematic diagnosis, but furthermore a response that is integrally associated with and routinely provided with the diagnosis.

U.S. Pat. No. 4,296,756 issued on Oct. 27, 1981 to Dunning and Enright for a "Remote Pulmonary Function Tester." It describes a remote pulmonary-function tester which interfaces to a central computer through telephone lines for review by an operator. This patent is limited to pulmonary testing—that is, to assessing the condition of the patient's lungs and the likely causes of any abnormalities detected.

Also serving as examples of inventions focusing on pulmonary function are U.S. Pat. Nos. 3,726,270 to Griffis et al., 3,896,792 to Vail et al., 3,977,394 to Jones et al., and 4,034,743 to Greenwood et al. Griffis' system transmits pulmonary data to a central location in real time to a central location, where the data "may be studied" by a "specialist." Vail's device does likewise, and it is commented that "such data can be evaluated with an eye toward earlier detection of disease and more effective treatment thereof . . . "

Jones provides a "computerized pulmonary analyzer" in which data from four pulmonary tests are automatically evaluated. As in most of the other inventions here under discussion, the "operator tells the test subject which breaathing maneuver he must follow for a desired test." It can be readily appreciated that such a procedure relies heavily on the patient's intelligent and active cooperation, and yields very questionable results when the operator cannot actually see the patient.

Greenwood seeks to provide "fully automated pulmonary function testing apparatus requiring relatively low levels of operator skill," but again at various points in the multifunction test procedure "the patient is asked . . . to breathe in a predetermined manner". For example, in one test the patient is expected to breathe "with maximal effort" against an obstruction; in another, "a patient inspires a full breath of pure oxygen and then expires at a substantially constant rate." Later the patient is told "to increase the rate of expiration" —and so forth.

Also among references cited in the prosecution of the Dunning application were U.S. Pat. Nos. 3,886,314 to Pori, 3,819,863 to Slaght, and 4,129,125 to Lester et al. The first of these relates exclusively to improvements in an eight-channel telemetering system for electroencephalographic data. The thrust of the invention is to facilitate communication between a remote data-system operator and "the resident doctor who is . . . applying electrodes from an EEG unit to the patient's head." From this it may be seen how far from a broad surveillance system Pori's device is, and how much individual on-site attention it demands.

Slaght's invention relates almost exclusively to electrocardiographic data. He introduces "a data transmitting terminal, primarily designed and intended for the coding of information relating to a patent, and of an electrocardiogram relating to that patient, for transmission via a communication line or link to a remote computer."

There are some systems that take one step in the direction of broader comprehensive screening, but it is a small step. Generally these systems collect plural-parameter data related to a particular malady as distinct from a particular organ. An example is the Lester patent, which focuses on crib death in infants. The invention is "an electronic monitoring device particularly suitable for babies," and that continuously monitors heart-beat rhythm, breathing rhythm, and temperature.

Lester's device "is preferably in the form of a belt having a buckle which houses the computer and memory. The unit is turned on by closing the belt into the buckle around the body of the patient. Should any of the patient's vital signs become abnormal, the electronic device . . . will sound the alarm alerting personnel near the patient that a failure has taken place. This will give persons near the patient ample opportunity to act on the patient in an attempt to restore breathing or other vital signs."

These excerpts from the Lester patent will be sufficient to show that the invention is (1) simply an acute-condition alarm system. That system is (2) limited to detecting vital signs, indeed a small number of such signs, and particularly to a highly simplified assessment of these few signs as against threshold criteria.

The excerpts also validate the earlier comments to the effect that the prior art is (3) narrowly focused on a particular medical problem, and (4) subject to a generalized assumption of suitable therapeutic response from "persons near the patient". In the broader problem area that is the target of my invention, it is to be generally assumed that there are no such persons.

Medical monitoring is a large field. To review here in detail a full cross-section of this field would be impractical, but in the preceding paragraphs I have discussed the prior art which appears to me most relevant to my invention.

1.2 BRIEF SUMMARY OF THE DISCLOSURE

The system described in this document is a home medical surveillance system (which will be abbreviated "HMSS" in the remainder of this document). It is a system for monitoring the state of health of ambulatory people in their homes. The HMSS is intended for those who know that they will—or suspect that they might—need the assistance of health professionals in the near future.

This invention allows for detailed physiological surveillance in the patient's home. Blood pressure, heart rate, ECG, respiration rate and depth, center-of-gravity shifts, weight, temperature, breathing sounds, shivering, conversational characteristics, average blood glucose, and relative cardiac output can be monitored.

This can be done in an extremely economical manner due to the minimal amount of trained, technical personnel time required per diagnostic session. Other interrelated services—paramedic, visiting nurse, and a new type of pharmacy—are also parts of this system.

The HMSS is based on a unique approach to monitoring physiological parameters. This approach requires minimal participation, training, knowledge, mental ability and cooperation by the person being monitored.

My invention encompasses both apparatus and method. This document describes the system of my invention as an apparatus, in terms of its components (each corresponding to a location where some of the instrumentation resides); and also as a method, in terms of a plan of operation.

More formally, my invention is a system of apparatus for home medical surveillance and response, for use by many subscribing patients—or, as they are sometimes called in this document, patient subscribers. The apparatus includes many patient subscriber apparatuses, each located in the home of one of such patients respectively.

Each particular patient subscriber apparatus includes some means for automatically sensing, with only passive cooperation by the patient, multiple parameters related to the state of health of the respective patient.

These parameters are such—and they are sufficiently numerous and sufficiently accurate—as to constitute in the aggregate a comprehensive profile of the patient's state of health.

For purposes of speaking generally, these means for automatically sensing parameters will be called "sensing means," and similar phraseology will be used for other components of the system.

Each patient subscriber apparatus also includes some means for automatically generating electronic health-parameter signals related to the parameters sensed by the sensing means. Each patient subscriber apparatus also includes some means for transmitting the electronic signals from the particular patient subscriber apparatus, and some means for receiving electronic signals.

The system apparatus also includes at least one surveillance and control office that is remote from the patient homes—or at least from most of them. The office is particularly adapted to interact with the many patient subscriber apparatuses. In particular, the office includes some means for receiving the electronic health-parameter signals transmitted from each of the patient subscriber apparatuses.

The office also includes some means for transmitting electronic signals to each of the patient subscriber apparatuses. To distinguish these transmitting means from the analogous components in the patient subscriber apparatus, those in the patient subscriber apparatus are called the "first transmitting means" and those in the office are called the "second transmitting means".

The office also includes some means for displaying indicia derived from the health-parameter signals that are received by the health-parameter signal receiving means. The indicia represent the health-related parameters for any selected one of the patients.

Also included in the office are some means for selecting a particular one of the patients for display of that particular patient's indicia by the displaying means. These selecting means are manually operable by a trained observer in the office.

The office also includes some means for generating the electronic signals for transmission by the second transmitting means to the patient subscriber apparatus.

The office also includes some means for accommodating the observer. These accommodating means are particularly adapted to afford the observer ready access to the displaying means and to the manually operable selecting and signal-generating means just mentioned.

In this system the trained observer is enabled to determine the general state of health of substantially each one of the many patients—and also to determine from this information whether a nonroutine therapeutic response should be provided for substantially each patient.

The office also includes mechanisms for entering the information about the patients' state of health into their respective medical records. It preferably also includes particular mechanisms for facilitating—and in certain urgent circumstances for actually providing—a nonroutine therapeutic response.

The sensing means in each particular patient subscriber apparatus preferably include a special diagnostic bed. This bed is formed to closely accommodate at least portions of the patient's body.

It carries sensors for at least several of the health-related parameters respectively—at specific positions in the bed that contact respective parts of the patient's body. These are parts of the body where respective health-parameter phenomena (to which the sensors are responsive) occur.

The sensing means also preferably include a special diagnostic chair. This chair carries sensors for at least two of the multiple parameters respectively. These are parameters whose measurement may be less than optimal when the patient is reclining. The chair sensors are at specific positions that in use adjoin respective parts of the patient's body—parts where respective health-parameter phenomena to which the sensors are responsive occur.

My invention is also a method of providing home medical surveillance and response, for use by many patients. The method includes the step of routinely obtaining a multiplicity of measurements related to the state of health of each patient, by remote sensing equipment, while the patient is at home—and with no more than passive cooperation by the patient.

The method also includes the step of receiving the results of all the routine measurements by remote data transmission into a central office, and displaying the results in the central office for routine review by an observer.

The method also includes the step of obtaining, in emergencies for any particular patient, a multiplicity of measurements related to the state of health of that patient while the patient is at home—again, with no more than passive cooperation by the patient.

The method also includes the step of receiving the results of all such emergency measurements by remote data transmission into a central office, and displaying the results of the emergency measurements for emergency review by the observer.

The method also includes the steps of determination by the observer, from the general state of health of the patient, whether a nonroutine therapeutic response should be provided—and, if so, at least facilitation by the observer of such a response.

The method of my invention also preferably includes the step of using a well-defined hierarchy of emergency priorities for a very large number of specific parameter ranges (and in some cases combinations of specific parameter ranges). This emergency-priority hierarchy guides the observer in a systematic way when he must select, from among two or more patients requiring emergency attention, which patient to deal with first, which next, and so on.

All of the foregoing operational principles and advantages of the present invention will be more fully appreciated upon consideration of the following detailed description, with reference to the appended drawings, of which:

2. DETAILED DESCRIPTION OF PREFERRED EMBODIMENTS: SYSTEM PHILOSOPHY

2.1 Reliability

The HMSS depends upon computers, modems, electronic record storage, and other modern instrumentation. All such equipment, however, is subject to more or less frequent faults and interruptions. Ordinary telephone lines, upon which the system depends for communication between components, are sometimes not sufficiently reliable for present purposes. This constitutes a grave danger when dealing with the critical care of patients.

The system addresses these dangers by redundancy, human supervision of all critical functions, and backup nonelectronic record keeping. In addition, all communications between components must be acknowledged by the recipient. Otherwise the message is not considered to have been received and the message is repeated until it is acknowledged (or alternate communications are established).

2.2 Priorities

It is expected that emergencies (situations requiring immediate reaction) will arise and be detected by the HMSS. When more than one emergency must be dealt with immediately, it is important that the resources of the HMSS be directed appropriately. The system is designed to handle such problems by directing responses in such a way that the most pressing affairs are attended to before less critical actions are undertaken.

Accordingly, a most important part of the system is an emergency priority hierarchy. This directs both computer and human observers to perform sequential activities according to a comprehensive priority procedure.

2.3 Patient Involvement

The HMSS is designed to require a minimum from the patient. It is expected that the patient (a) be ambulatory, (b) can communicate in a language spoken by system operators, (c) can lie down on a special diagnostic bed, (d) can look into an optical analyzer that determines blood-glucose concentration, (e) can place his arm into a blood pressure cuff, and (f) can remove and self-administer medicines from a medicine dispensary.

2.4 Record Keeping

Records are kept of all system interactions. These include, but are not limited to, data acquisition, observer comments (e. g., diagnoses), emergency reactions, system element responses, orders, and maintenance records. These records are maintained in electronically retrievable form at each pertinent location, as well as in permanent (written) form at a surveillance and control office (SCO). Also, selected permanent records are kept in the physician's office.

2.5 Patient/Physician Relationship

The system will only accept patients of physicians whose offices are equipped with our computer instrumentation. The patient is considered to be under the care of his private physician, not the HMSS. The system collects physiological data and only intervenes in an emergency when the patient's physicians are unavailable immediately, or in the case of a "super emergency" when seconds count.

3. DETAILED DESCRIPTION OF PREFERRED EMBODIMENTS COMPONENTS

Figure 1:
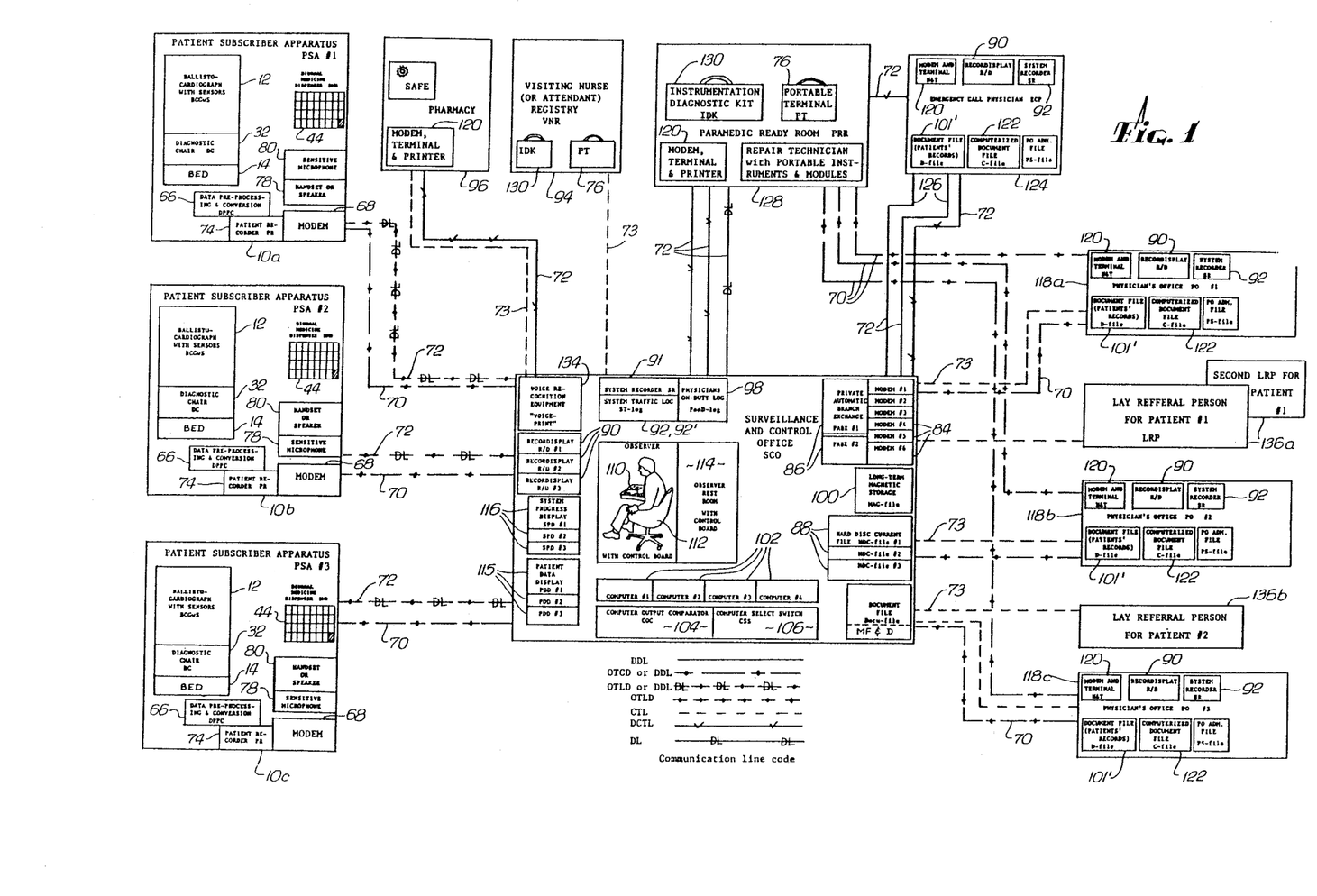
FIG. 1 is an overall schematic diagram of the apparatus of my invention.

The following discussion may be best understood with reference to FIG. 1.

3.1 PATIENT SUBSCRIBER APPARATUS (PSA)

A patient subscriber apparatus 10a, 10b, 10c, etc. (PSA) is located in the home of each subscribing patient, and is the collection of devices listed below. These devices elicit a wide variety of clinical signs.

3.1.1 DIAGNOSTIC BED

This consists of a radically new kind of ballistocardiograph with built-in sensors 12 (BCGwS) which forms the heart of the PSA. The ballistocardiograph (BCG) itself is a device for estimating relative cardiac output and force of contraction of the heart. It also measures breathing rate, estimates depth of respiration, detects shivering, and determines the patient's weight and changes in center of gravity (c. g.).

It is a bed 14 (see FIGS. 2-4), preferably consisting of a mold 16 of the patient's body, made of rigid, light, porous plastic. The patient lies in the bed for about a minute while the sensors in the bed make automatic health-parameter measurements.

Figure 2:
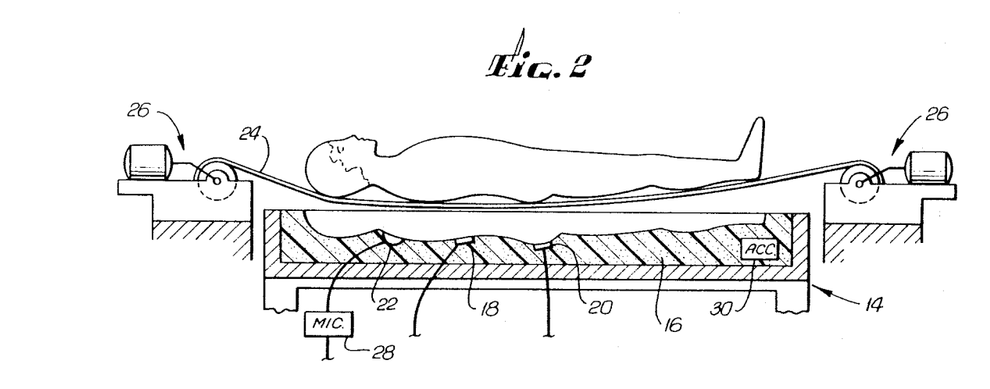
FIGS. 2 and 3 are side elevations, partially in section, of the diagnostic bed of my invention, showing the bed in different conditions of use by a patient. For clarity in these drawings the patient's arms are not shown.
Figure 3:
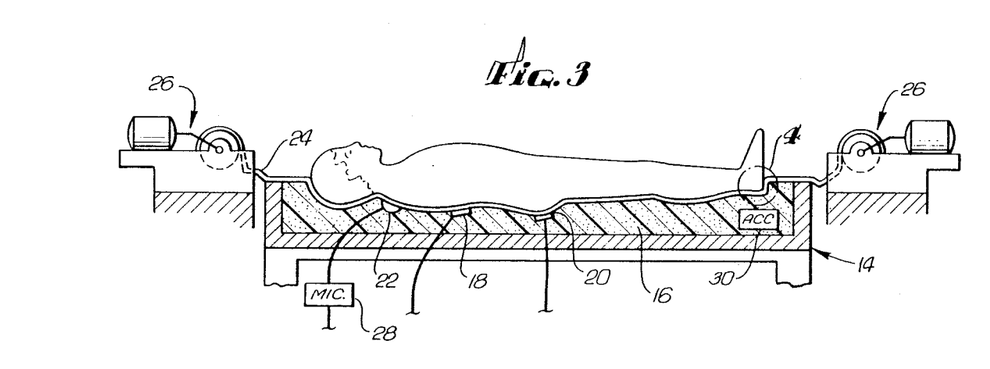
Figure 4:
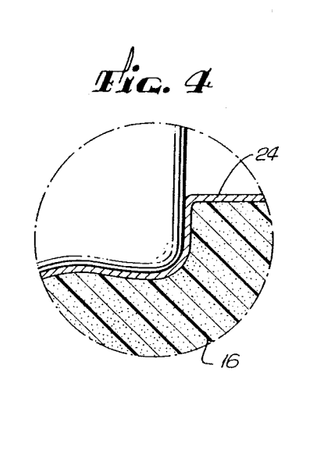
FIG. 4 is a similar view of a portion of FIG. 3, enlarged to show more clearly the functioning of a particular part of the bed.

The BCG measures the minute pulsations due to the heart's pumping action and the intake of air. These pulsations are recorded as a ballistocardiogram which may be compared to a stored baseline BCG to estimate changes in relative cardiac output and other parameters.

One set of sensors attached to the BCG detects the electrocardiogram (ECG). These are conductive plastic electrodes 18 which make contact with the bare back of the patient. From the electrocardiogram, heart rate is determined. Cardiac malfunctions can be detected by comparing the ECG to a stored baseline ECG.

Other sensors include (a) transthoracic impedance-pneumography electrodes, which give information on breathing; (b) thermistor temperature sensors 20, embedded in the surface of the mold at points corresponding to the popliteal fossae, to provide the patient's temperature; and (c) strategically placed stethoscope bells 22 embedded in the mold, to detect sounds indicative of lung problems (rales or asymmetrical sounds).

Entry of the patient into the molded depression in the bed—and exit of the patient from the depression—must be effected gently and consistently, to avoid damaging the sensors and to enhance reproducibility of the measurements. These requirements would be somewhat difficult for an unaided patient to satisfy—because the depression engages the patient's body very closely, and also because many patients are partially disabled.

Accordingly the apparatus of my invention preferably includes a hammock 24 (FIG. 2) that can be held taut above the bed by a dual motor-and-roller mechanism 26. The patient's body can be maneuvered onto the taut hammock with relative ease.

After the patient is in position on the hammock, the patient (or the observer, by remote control) actuates the mechanism to allow the hammock to become flaccid—and thus to lower (FIGS. 3 and 4) the hammock and patient together into the depression. After the portion of the diagnostic session that involves the diagnostic bed, the patient (or observer) actuates the mechanism to raise the hammock and patient together out of the depression in the bed, so that the patient can get up—again with relative ease.

FIG. 2 also shows exemplary positions of certain of the electrodes and other sensors—such as a microphone 28 that acts as a stethoscope, and such as thermistor 20 that acts as a thermometer.

The hammock has reinforced holes placed to allow contact of the various sensors with the patient's skin, to the extent required.

Ballistocardiograph accelerometers 30 may be embedded in the mold, or attached to the mold—or a strain sensor may be attached between the mold and an object fixed relative to the ground. Other sensor arrangements will occur to a person skilled in ballistocardiograph configuration.

To preserve the operation of the bed as a ballistocardiograph, the bed itself should be supported in such a way as to be free to move longitudinally. This condition may be achieved in any of a great variety of ways. For example, the bed may be hung from above by wires, or may rest upon slippery horizontal linear bearings. Alternatively it may be supported by vertical legs which constrain it to move only longitudinally.

In any of these systems, it is preferable to provide four (or at least three) independent suspension points, which can each be instrumented to provide the center-of-gravity measurement mentioned earlier.

Figure 5:
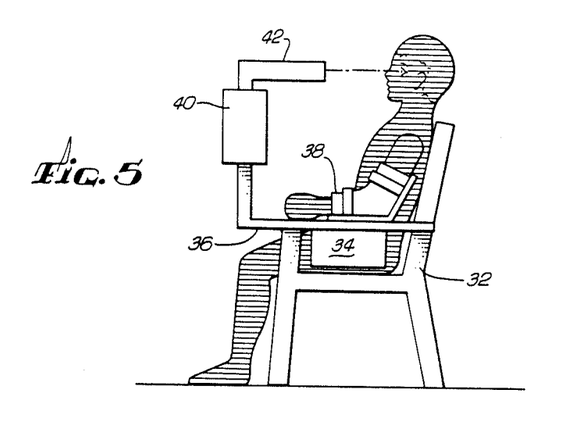
FIG. 5 is a perspective schematic view of one embodiment of a diagnostic chair.

3.1.2 Diagnostic Chair (see FIG. 5)

This is a chair 32 to which are attached instruments that estimate average blood-glucose concentration and measure arterial blood pressure. A Doppler ultrasonic arterial automatic blood pressure (DUSIAP) machine 34 is utilized for the latter measure.

The patient sits in the chair and positions his arm in a guide channel on a special arm rest 36, equipped with a "clamshell" cuff 38, such that the cuff can close around the arm. This instrument automates the traditional physician's sphygmomanometer (greatly improved by the doppler ultrasonic arterial wall motion detector).

An optical glycometer 40 (OG) is attached to the same chair. The patient looks into an ocular device 42 that measures changes in the refractive power of the eyes. This measure is directly related to the average blood-glucose concentration over the course of about a day. The optical glycometer measurement is calibrated initially against laboratory results of blood glucose. Thereafter, for that patient, average blood-glucose concentrations are readily estimated from the measurement of the optical glycometer.

Figure 6:
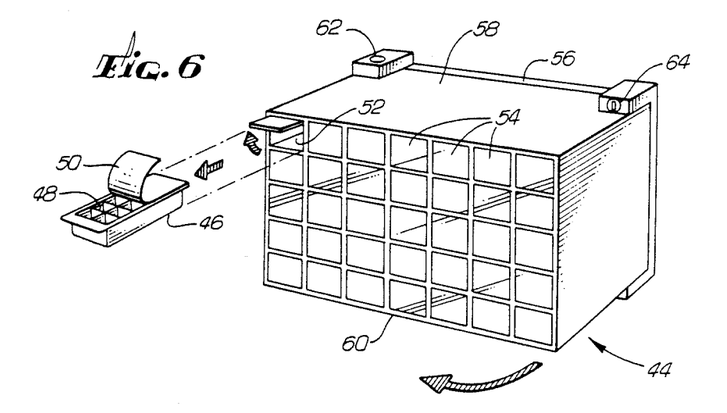
FIG. 6 is a perspective view of one embodiment of a daily medicine dispensary.

3.1.3 Daily Medicine Dispensary (DMD) (see FIG. 6)

A daily medicine dispensary 44 (DMD) allows the patient access to each day's supply of medicine during each 24-hour period. The medicines are prepackaged in sealed transparent trays 46, sections of which are labeled with the time of day at which the medicines are to be taken. A month's supply of medicines is packaged, delivered, and loaded into the DMD by the pharmacy (its major function). The DMD also sends messages to the surveillance and control office (SCO) indicating that the medicine tray for that day has or has not been removed.

An emergency oxygen supply can be maintained (by the pharmacy) at the PSA if ordered by the patient's physician.

The daily doses of medicines (as many as fifteen different kinds for some patients, including vitamins) are put up by the system pharmacy in special disposable trays 46 with individual pockets (like an ice cube tray). An easily removable paper cover 50, sealed to the rims of the tray and adapted to be "peeled" back one pocket at a time, holds the pills in place. Written above each pocket on the paper cover are the day of the week, date and time of day when the corresponding dose should be taken.

This special tray is loaded into the DMD by pharmacy personnel who visit the patient's home for the purpose. The DMD senses the presence or absence of the tray and, upon interrogation by the SCO, signals whether the tray has been removed.

The DMD consists preferably of a wall-mounted unit containing at least thirty-one compartments 52 (nests), each closed in front with a door 54 sealed by a mechanism which allows only one door (each successive door) to be opened each day at any time after a particular time of day. Each door is marked with the day of the month (From "1" to "31").

The unit is preferably constructed in two separate portions—(1) a rear panel 56 and (2) a front case 58 that encloses the medication, the multiple doors just mentioned, and the electronics 60. The rear panel is wall mounted. The entire front case is hinged to the rear panel, with the line of hinge pins 62 vertical. A lock 64 is provided to keep the front case tightly closed against the rear panel—the normal condition for use by the patient, who removes medications only through the individual doors in the front case. When the lock is unlocked the front case may be swung away from the wall, exposing the rear of all the nests for refilling (see FIG. 6).

3.1.4 Data Acquisition and Transmission

All of the devices of the PSA send data to a data preprocessor and converter 66 (DPPC). The DPPC converts the data to a form amenable to transmission by modem 68 over a telephone line to the SCO. (The phone line can be an ordinary telephone line 70 TL or, if the patient desires, a dedicated line 72). Outgoing data are stored in electronic form by a patient recorder 74 (PR). This electronic record is not generally accessible to the patient. However, paramedics or repair personnel can retrieve these data if necessary with the use of a portable terminal 76.

Figure 7:
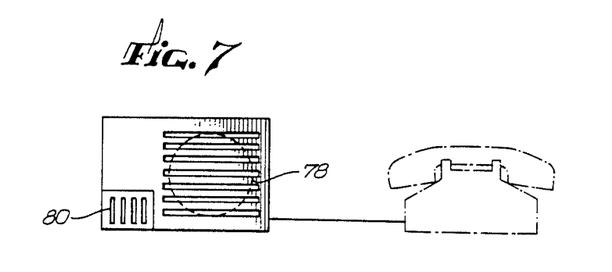
FIG. 7 is a front view of one embodiment of means for making voice communication with a patient, including a sensitive microphone.

3.1.5 Communications (see FIG. 7)

An option on the PSA is a telephone line with a speaker attachment 78 and a sensitive microphone 80, permitting the observer in the SCO to converse with the patient while going through the diagnostic procedure. The SCO can, of course, be reached over ordinary telephone lines. The datient must have a phone in or near the room where the PSA is housed.

3.2 SURVEILLANCE AND CONTROL OFFICE 82 (SCO)

3.2.1 Data Receipt and Transmission

Data from the PSA's are received over TL's or DCTL's through modems 84 and are routed through a redundant private automatic branch exchanger 86 (PABX) in the SCO (see FIG. 1). Data are processed immediately upon receipt and are displayed to an observer. The SCO transmits the raw and processed data to the physician as soon as possible, together with a report of the actions of the system, if any.

All transmissions of raw data to the SCO are recorded in both electronic form and in "hard copy." A hard-disk current file 88 (HDC-file) is kept in duplicate. A third hard-disk file (HDC-file #3) is maintained as a backup for HDC files #1 and 2. Record-and-display units 90 (R/Ds) make permanent written records of the diagnostic sessions (Docu-file).

Relevant nonphysiologic patient information can also be sent or received by modem transmission. Updated patient files from physicians and reports from nurses and paramedics can be sent this way. For the sake of patient safety and system efficiency analysis, a record of all transmissions is kept in a system traffic recorder log 92 (ST-log).

3.2.2 Other Communication Methods

Besides the dedicated communications telephone lines (DCTLs) to patients and physicians, and certain dedicateddata lines (DDLs), the SCO has a number of telephone lines (TLs), including ordinary telephone lines for data (OTLD). These are used to communicate with a visiting nurse registry 94 (VNR), with the pharmacy 96, and if necessary, with patients and physicians. These can double as modem lines if the expense of a dedicated line must be avoided.

3.2.3 Records

In addition to patient records, a number of records of the actions of the system are kept. A system-traffic recorder log (ST-log) is a record of all transmissions to and from the SCO. A physicians-on-duty log 98 (PonD-log) records the times at which physicians sign in and out. A record of instrument calibration and preventive maintenance is constantly updated.

Electronic records of raw data are maintained in duplicate on hard disks for a time for easy access and evaluation. Periodically, these records are transferred to magnetic tape 100 for long-term storage (Mag-file).

Important details of all patients in the system, stored in instantly retrievable, reduced photographic form (microfiche), are constantly updated. This microfiche file and display (MF&D) unit 101 is available to the observer and to an emergency call physician (ECP).

3.2.4 Data Reduction and Computer Analysis

In order to obtain certain clinically useful values from the data gathered at the PSA, a number of calculations must be made. These are handled by the computers 102 at the SCO. The computers also have baseline or normal measurements in memory and display the new data with the displayed stored data. If the new data show significant changes, the observer initiates the appropriate system reaction (section 4.4).

There are at least four computers in the SCO for this purpose. One is maintained as a backup while the others are calculating results from the incoming data. These three are performing the same calculations on the same data. A computer-output comparator 104 (COC) compares the results produced by three computers respectively. Should the results from any computer vary from the results from the other two, that computer is bypassed by a computer-select switch 106 (CSS), and an automatic diagnostic test sequence is initiated.

3.2.5 Data Interpretation by Observer

Much of the information obtained by the system is not amenable to computerized analysis. The observer is essential for the interpretation of these data. The ballistocardiogram, electrocardiogram, impedance pneumogram and DUSIAP trace must all be interpreted by a professional (the observer, or "intensivist") who compares the new data to the stored baseline tracings. Also, lung sounds require human monitoring. Voice interaction with the patient is another important function of the observer.

3.2.6 Observer's Station

A observer's station 108 consists of the displays and logs of system activities, the control board 110 (with attached computer keyboard) that initiates certain set sequences of system responses, a chair 112 or the like, and a rest room 114 (also equipped with a control board), situated so that the displays are visible from within.

There are at least three record-and-display units (R/Ds) and at least three patient-data displays 115 (PDDs) for incoming patient data; two of each type of display may be active at any time, while the third serves as a backup. Each R/D displays the instrument traces (BCG, ECG, DUSIAP and impedance pneumogram) of the incoming data, together with the corresponding patient's baseline traces. The PDD displays relevant nonphysiological data (e. g., patient name and address) as well as data calculated by computer (e. g., weight, average blood glucose concentration, heart rate). The microfiche file and display (MF&D), is nearby and serves as a backup for baseline values.

There are also three system progress display units 116 (SPD) used during emergencies—one for each of three patients whose emergency conditions are at the top of the system's emergency-priorities hierarchy. The SPD is a video display of the current status of emergency measures taken by the system. The system-traffic log (STL) and physician-on-duty log (PonD-log) are also visible from the observer's chair.

The control board is a panel of approximately fifty buttons, each of which is illuminated from within when active, that is immediately adjacent to the observer's chair. These buttons each initiate a preprogrammed sequence of events. For example, one button will initiate simultaneous calls to the paramedics and to the distressed patient's physician, thus reducing response time. The attached computer keyboard is used to enter observer comments to the record of the diagnostic session.

The rest room for the observer is directly behind the observer's chair. The rest room is built on a raised platform. A window is built into the room so that the observer may look down and see the various displays, while the observer's privacy is insured.

3.3 PHYSICIAN'S OFFICE 118a, b, c (PO)

HMSS will only accept patients of subscriber physicians whose offices are equipped with the HMSS instrumentation. This includes a record-and-display (R/D) unit, similar to the one used in the SCO by the observer, a modem, a display terminal 120, and a personal computer.

3.3.1 Data Transmission and Receipt

A copy of the data received by the SCO from the PSA is sent to the patient's physician. It is stored electronically in a computerized file 122 (C-file) and in hard-copy form (by the record-and-display). The physician is expected to examine the data from each diagnostic session and to add the hard copy to his own file of the patient. As with any transmission from the SCO, receipt of the data must be acknowledged.

3.3.2 Acceptance of Call Duty

Whenever a primary or alternate physician "signs off" (i. e., will not be available for a specified time period for emergency calls), he must notify the SCO, either over the data lines or by voice communication, that his patients are to be under the care of another, designated, alternate subscriber physician for that period of time.

The alternate physician must validate (accept) this assignment for the "sign-off" to be valid. Similarly, the alternate cannot "sign-off" until the assignee validates his acceptance.

Thus a record, the physician-on-duty log (PonD-log), is kept indicating which physician is or was responsible for which patients at what time and date.

3.4 EMERGENCY-CALL PHYSICIAN'S OFFICE 124

This office may be in the SCO.

3.4.1 Communications

The system will have available, around the clock, an emergency-call physician (ECP) to respond to emergencies should a patient's physician (and back-up physicians) be unavailable. The ECP's office has the same equipment as a physician's office so that the ECP may examine relevant data. The terminal is connected to the SCO via a dedicated data line 126 (DDL). There is also a dedicated communications telephone line (DCTL) to the SCO for voice communications. Finally, there is a DCTL to a paramedic ready room 128.

3.4.2 Records

Important details of all patients in the system, stored in instantly retrievable, reduced photographic form (microfiche), are constantly updated. This microfiche file and display is available to the emergency-call physician should a computer breakdown occur.

3.5 PARAMEDIC READY ROOM (PRR) 128

The PRR should be in the same building as, if not immediately adjacent to, the SCO, so that a private dedicated line (PDL) can connect them.

3.5.1 Communications

The PRR is connected via dedicated communication telephone lines (DCTLs) to both the SCO and the ECP's office. A PDL also connects the PRR to the SCO. Other physicians can reach the PRR via ordinary phone lines. Paramedics can be reached in the field via radio.

3.5.2 Portable Terminal 76 (PT)

This device allows the paramedics to communicate with the SCO's computers at the patient's home. In emergency, patient data can be readily obtained through the modem of the PSA. The portable terminal is also used to extract information from the electronic storage device of the PSA.

3.5.3 Instrumentation Diagnostics Kit 130 (IDK)

The paramedics also carry an instrumentation diagnostics kit 130 which is used to calibrate and maintain the devices in the PSA.

3.6 VISITING-NURSE REGISTRY 94 (VNR)

The VNR is offered as a part of the HMSS for the sake of completeness in home health-care services. Subscribers may or may not wish to make use of it.

3.6.1 Communications

The Registry has no special communication devices, since it does not generally function during emergencies. It can be reached by ordinary telephone lines.

3.6.2 Portable Terminal

When appropriate, nurses attending the patient subscribers can take with them a portable terminal in order to obtain patient information from the SCO.

3.7 PHARMACY 96

The main function of the pharmacy 96 is to package and replenish the medicines of the daily medicine dispensary (DMD). As the use of some of these medicines is regulated, the pharmacy has a safe for the proper storage of these medicines. The pharmacy also delivers oxygen tanks for those subscribers who require an emergency oxygen supply.

The pharmacy maintains a log (computerized and hard-copy) of all prescriptions and replenishments of DMD's. This log is transmitted via modem to the SCO, where it is duplicated.

Verbal prescriptions should be confirmed before they are filled. To this end, a voice recognition machine 134 ("voice-print"), housed in the SCO, confirms that the voice over the phone does indeed belong to the physician. If the voiceprint is at this time insufficiently simple to use, each subscriber physician will confirm his identity by a special code system.

3.8 LAY REFERRAL PERSON 136a, b, c, etc. (LRP)

This is a friend, guardian, or relative who is notified of events as specified by the subscriber; for example, if the patient requires emergency hospitalization. The LRP 37 is not generally notified of routine responses of the HMSS. The patient subscriber may have several LRPs.

4. DETAILED DESCRIPTION OF PREFERRED EMBODIMENTS: PLAN OF OPERATION

4.1 DIAGNOSTIC DATA ACQUISITION

4.1.1 Routine Diagnostic Session

Routine diagnostic sessions are scheduled on a regular basis for each patient. This can be on a monthly, weekly, or even daily basis as required and prescribed by the subscriber physician. A session will take less than ten minutes of a patient's time, but must occur at the agreed time.

The diagnostic session begins in the diagnostic bed. A few minutes before the scheduled time, the patient lies down in a hammock (FIG. 2) that is stretched taut over the diagnostic bed. The hammock gently lowers the patient into the molded plastic (FIG. 3) of the bed. Due to the extreme sensitivity of the instrument, and so that the patient may be in a resting state, a few minutes must be allowed before recordings are started.

At the time scheduled for the diagnostic session, the observer in the SCO calls the PSA and establishes voice communication with the patient over the annunciator.

The patient then activates the BCGwS by pressing a button, molded into the plastic, underneath the index finger of one hand. (Should the patient be unable to operate the BCGwS, or the other devices of the PSA, the observer can control their operation from the SCO.) The sensors then begin to collect data which are sent to the SCO via the DPPC and the modem in the PSA. During this period, the patient must remain as still and quiet as possible.

In the SCO, the observer examines the traces from the BCG, ECG, and impedance pneumogram. First, the observer checks the quality of the data. Excessive movements by the patient may make the BCG unusable. Improper contact of the electrodes may invalidate the ECG. If the data contains artifacts, the observer may ask the patient to repeat or prolong the session.

Second, the observer examines the traces for untoward signs. Some are visible immediately, while others require the observer to compare a trace to a baseline which has been stored electronically and is displayed side by side with the newly recorded traces. A microfiche file of baseline traces and other patient information is available as a backup. The observer's reaction to untoward signs is described in section 4.4.

Normally (that is, in the absence of a clear emergency) the observer will next notify the patient that collection of data from the diagnostic bed is completed. The patient will then press another button, built into the mold—or the observer will actuate one of the controls at his console—to tighten the hammock, raising the patient slightly out of the mold and allowing the patient to leave the bed easily.

The patient then sits on the diagnostic chair, places his arm on a special arm rest in a channel provided and into the DUSIAP clamshell cuff. He then moves the optical glycometer into position and peers into it. The clamshell cuff is closed, the DUSIAP cycling commences, and data from the DUSIAP and RG are transmitted to the SCO. Again, the observer checks the quality of the data and examines it for any untoward signs.

The optical glycometer readings are multiplexed with the DUSIAP readings. In order to obtain a valid measure of blood pressure, the DUSIAP executes at least five one-minute measurement cycles. The number of cycles can be increased by the observer (after notifying the patient of the lengthened session).

If there are no untoward signs, this is communicated to the patient. The patient is also notified that the present results are tentative and that the patient's private physician will subsequently analyze the data and send a report.

Should the observer note untoward signs during a routine diagnostic session, he may ask the patient to repeat certain of the diagnostic tests for confirmation of the signs. The actions of the observer will depend on the severity of the signs, as detailed in Section 4.4. Conversation with the patient will help estimate the urgency of the situation.

4.1.2 Emergency Diagnostic Session

The patient may request an emergency diagnostic session at any time. The patient notifies the SCO that he feels this is necessary, and begins the session as described above.

The Observer will put on "hold" all patients undergoing routine sessions in order to devote full attention to the emergency. The observer's actions during emergency sessions are more fully described in section 4.4.

It is assumed that such a request constitutes a potential emergency and the system reacts accordingly. Since an emergency disrupts diagnostic sessions in progress, it is expected that the patient subscribers use the same discretion with the system that they would with public services.

4.2 DIAGNOSTIC DATA PROCESSING, EVALUATION, AND RECORDS

4.2.1 Calculation of Relevant Clinical Values

The following parameters are calculated by the computers in the SCO:

Heart rate (HR) from ECG
ST depression or elevation from ECG
Center of gravity from respective BCG weight transducers on individual support legs of the BCG
Patient weight from BCG weight transducers
Breathing rate and depth from impedance pneumogram and/or BCG
Temperature from thermistor in diagnostic bed
Average blood glucose concentration from optical glycometer.

4.2.2 Display of Relevant Clinical Values and Instrument Traces

The calculated data (above) are displayed on a physiologic data display (PDD) together with baseline values for that patient. Relevant patient history and other non-physiological data are displayed concomitantly. BCG, ECG, DUSIAP and impedance pneumogram traces are written by the record-and-display unit (R/D). The R/D draws the incoming traces and the stored baseline traces simultaneously, so that the two may be compared directly. (Present video screens are too narrow to handle the tracings required here.) The baseline traces are also available on the microfiche display (MF&D).

4.2.3 Evaluation of Data by Computer

For parameters that the computer can calculate, the computer also compares to baseline values. If these values deviate from baseline, that is, constitute an untoward sign by the criteria established for that patient, the computer indicates this to the observer, along with audible (beeps) and visible (flashing numbers) cues. Note that the computers in this system handle only the readily calculated digital values.

4.2.4 Evaluation of Data by Observer

Certain data are not amenable to computer calculation. The observer must evaluate the traces from the BCG, ECG, DUSIAP and impedance pneumograph, the sounds from the stethoscope, and vocal communications with the patient. Perhaps most importantly, the observer is charged with estimating the quality of the traces.

Artifacts in the traces may occur due to a variety of reasons, from telephone-line static or instrument malfunction to incorrect operation of the instruments by the patient subscriber. The system addresses these problems by the use of dedicated phone lines (where affordable) and by the use of rugged, reliable, and simply operated instruments.

The observer evaluates these data, as well as the data calculated and provided by the computers (above) for untoward signs. These signs, evaluated only by the observer, include:

Blood pressure from DUSIAP
Relative cardiac output from BCG
ECG abnormalities (PVC's, fibrillation, etc.) from ECG
Breathing sounds
Shivering from BCG
Voice communications with patient.

4.2.5 Storage of Data

As data are received from the PSA, they are recorded on the record-and-display. This hard copy constitutes the permanent record of data. The traces are also digitized and stored in electronic form (on hard disk) for more convenient and rapid retrieval of the information. The hard-disk record is kept in duplicate. Periodically, all collected data are recorded on magnetic tape, floppy disks, or the like for permanent storage and to make room on the hard disks for new data.

4.3 EMERGENCY PRIORITY HIERARCHY

Priority in this context means the order in which various untoward signs, noted by the observer, are handled, should more than one emergency occur at the same time. For all of the untoward signs indicated here, some response from the surveillance and control office must be initiated as soon as practical.

The SCO responds first to the emergency with the highest priority (lowest number), then to the emergency with the second highest priority, and so forth. The range limits listed below may be adapted to the individual patient by order of the patient's physician.

| Group | Signs | Range Limits | Priority |
|---|---|---|---|
| | | 4.3.1 Untoward Vital Signs | |
| Heart rate | | | |
| | Bradycardia | | 3 |
| | | (67% of baseline heart rate, or less) | |
| | Tachycardia | | 3 |
| | | (133% of baseline heart rate, or more) | |
| Blood pressure | | | |
| | Hypertension | | 3 |
| | | (systolic rise to 125% of baseline) | |
| | Hypotension | | 3 |
| | | (systolic drop to 75% of baseline) | |
| Relative cardiac output | | | |
| | Cardiac output low: | | |
| | | 65% of baseline flow, or less | 2 |
| | | between 65% and 75% of baseline flow | 3 |
| | Cardiac output high | | |
| | | (150% of baseline flow, or more) | 3 |
| Temperature | | | |
| | Hyperthermia: | | |
| | | increase of 3.5° C., or more | 2 |
| | | increase between 1.5 and 3.5° C. | 4 |
| | | increase of 1.5° C., or less | 5 |
| ECG | | | |
| | Auricular (atrial) fibrillation or flutter - increase | | 3 |
| | Bigeminy | | 2 |
| | ST depression (at 10 mm = 1 millivolt): | | |
| | | decrease of 2.8 mm, or more | 2 |
| | | decrease between 1.5 and 2.8 mm | 2 |
| | | decrease of 0.8 to 1.5 mm | 3 |
| | ST elevation: | | |
| | | increase of 2 mm, or more | 2 |
| | | increase between 1 and 2 mm | 3 |
| | PVCs (cardiac arrhythmias) above baseline: | | |
| | | 6 per minute, or more | 2 |
| | | 3 to 5 per minute | 3 |
| | | 2 per minute, or fewer | 4 |
| | Ventricular fibrillation | | 1 |
| | Ventricular tachycardia | | 1 |
| Breathing | | | |
| | Apnea (30 seconds without a breath) | | 1 |
| | Bradypnea | | 3 |
| | | (50% of baseline breathing rate, or less) | |
| | Tachypnea: | | |
| | | 200% of baseline rate, or more | 2 |
| | | between 133% and 200% of baseline rate | 4 |
| | Breath sounds asymmetrical | | 3 |
| | Rales | | 3 |

| Group | Signs Range Limits | Priority |
| --- | --- | --- |
| Other | | |
| | Center of gravity change (more than 10 inch-pounds of moment) | 3 |
| | Hyperglycemia (substantial "myopia" increase): | |
| |     glucose 300 milligram-%, or more | 4 |
| |     glucose between 200 and 300 milligram-% | 5 |
| | Shivering: | |
| |     severe | 2 |
| |     mild | 3 |
| | Weight gain | 5 |
| | Weight loss | 5 |
| 4.3.2 Other Untoward Signs | | |
| Voice Communications | | |
| | Absence thereof | 4 |
| | Alarming or emergency (patient-initiated) | 2 |
| | Mild complaint | 5 |
| | Significant problem, but not emergency | 4 |
| Equipment problems | | |
| | BCG blocked (Patient does not exit from BCG in allotted time.) | 5 |
| | BCG empty (Patient does not enter BCG in allotted time.) | 5 |
| | BCG maloperative | 4 |
| | BCG - patient offset (Patient is not properly "seated" in BCG.) | 5 |
| | Breath sounds device maloperative | 5 |
| | DUSIAP maloperative | 4 |
| | ECG device maloperative | 4 |
| | Medicine of this day not removed from DMD | 5 |
| | Medicine not removed for two or more days | 2 |
| | Modem maloperative | 5 |
| | Optical glycometer nonoperative | 5 |
| | Temperature device maloperative | 5 |
| | Weight/c.g. device maloperative | 5 |

4.3.3 Multiple Untoward Signs

Certain combinations of untoward signs warrant emergency priorities higher than the individual signs taken singly. These are listed below and constitute part of the Emergency Priority Algorithm.

| | |
| --- | --- |
| Cardiac output high, and fever (septic shock) | 2 |
| Change in c.g., and heart rate increased above 150% of baseline (bleeding) | 1 |
| Change in c.g., and heart rate decreased below 67% of baseline (bleeding) | 1 |
| No voice communication, and no data | 1 |
| No voice communication, and shivering | 1 |

4.4 OBSERVER'S INTERACTION WITH PATIENT

4.4.1 During Routine Surveillance

As described above, the observer is in voice communication with the patient during diagnostic sessions. The observer guides the patient through the session, if required, and informs him of the tentative results at the end of the session.

If the observer notes untoward signs, he establishes a conversation with the patient in order to obtain further indications of distress, if any. These symptoms, as related by the patient, are noted in the patient record for transmission to the patient's physician.

If the signs are sufficiently severe to warrant reaction from the system, the observer initiates the appropriate system response. Untoward signs with priority levels of "2" through "5" indicate an emergency and require the system to immediately contact the patient's physician, who will initiate whatever actions are necessary.

The priority level "1" indicates a higher level of emergency, and calls for immediate action on the part of the paramedics. In such an instance, the system notifies them first, and then the patient's primary physician.

4.4.2 During Emergency

Upon receipt of an emergency signal from any patient subscriber, the observer turns on an automatic announcer which informs any patients undergoing routine sessions that their sessions are being interrupted and to await further instructions. The observer can then devote full attention to the emergency call, initiating voice communication with the distressed patient.

If the patient seems ill but not critically so, and is able to participate in a diagnostic session, then a session is initiated. While the patient is getting into the diagnostic bed, the automatic calling system attempts to contact the patient's physician. The incoming data are automatically transmitted to the subscriber physician's recorder system.

If, however, voice communication indicates that emergency action is required immediately, the observer may first contact the paramedics, and then institute the normal procedure for reaching the patient's private physician. In such a case there may not be time for nor purpose to a diagnostic session.

4.5 PARAMEDICS

4.5.1 Responsibilities During Emergencies

HMSS's paramedics respond to emergencies in the same manner as do public paramedics. Since they are part of the system, they will know, before arriving at the scene of an emergency, what to expect and the special requirements of the patient. In the event that several emergencies requiring paramedics occur at once, the regular, public paramedic services are contacted.

4.5.2 Responsibilities at Other Times

The system's paramedics calibrate, test and maintain the diagnostic equipment in the PSA. When in the field, they can be reached by radio should an emergency arise.

5. DETAILED DESCRIPTION OF PREFERRED EMBODIMENTS: APPENDICES

5.1 Glossary

Ballistocardiograph with sensors 12 (BCGwS). See "Diagnostic bed."

Baseline. For the purposes of this document, a baseline value or trace is one that is typical of the normal, resting state of the patient. It is the value or trace against which data from a diagnostic session is compared.

Blood-pressure and glucose chair 32 (BPGC). See "Diagnostic chair."

Center of gravity (c. g.). As used in this document, the center of gravity is located on a vertical line, generally passing near the navel, about which the supine body would be perfectly balanced if it could be stiffened and rested upon a fulcrum.

Communication telephone line 73 (CTL). Normal telephone line for verbal communication.

Computer output comparator 104 (COC). A device (in the SCO) that constantly checks the accuracy of the several redundant computers by comparing their outputs with each other. It signals a warning when any deviation between outputs occurs.

Computer select switch 106 (CSS). Switches that disconnect a working computer should it malfunction, and connect a properly functioning computer into the working system.

Computerized file 122 (C-file). The electronic file, in the physician's office, of raw and processed data from diagnostic sessions.

Daily medicine dispensary 44 (DMD). A device (part of the PSA) that allows only one daily dose of pills to be accessed in a twenty-four-hour period. It also, upon interrogation, informs the SCO whether the daily medicine has been taken from the dispensary.

Data preprocessor and converter 66 (DPPC). This device (part of the PSA) controls and collects the data from the BCGwS, BP+SC, and DMD, and converts the data to a form appropriate for modem transmission.

Dedicated line 72,721. A telephone line that is routed through the telephone company, but does not go through the normal switchboard. Instead, the line is "hardwired" and is not susceptible to failures of the switching equipment.

Dedicated communication telephone line 72 (DCTL). This is a DL for verbal communication. This is not routed through the telephone company switchboard.

Dedicated Data Line 721 (DDL). This is a DL strictly for data transmission.

Diagnostic bed 14. This device (part of the PSA) is a radically new type of ballistocardiograph (BCG) to which are attached sensors of physiological parameters. The BCG measures the forces on the body due to the pulsation of blood. Relative cardiac output and force of cardiac contraction are estimated from these data. The sensors (not part of the ballistocardiograph per se) detect ECG, rate and depth of breathing, lung sounds, temperature, weight, center of gravity and shivering.

Diagnostic chair 32. This chair has attached to it devices for the estimation of systolic and diastolic arterial blood pressure (by Doppler ultrasonic arterial wall motion detection) and blood glucose (by measurement of the patient's eye optical power).

Document file 1011 (D-file, Docu-file). The patient record, kept in the physician's office.

DUSIAP 34. An automatic machine for noninvasively determining systolic and diastolic blood pressures. It uses a Doppler ultrasonic arterial wall motion detector which gives reliable readings even under conditions of surgical shock.

Emergency-call physician (ECP). The physician (or physicians) available round-the-clock to handle emergencies if neither the patient's physician nor his alternate can be reached.

Hard-disk current file 88 (HDC-file). Redundant (i. e., two independent disks with the same data) computerized file system for recently acquired data.

Home medical surveillance system (HMSS). The system (1) composed of all machines and interconnections described in this document, especially, but not exclusively, the PSA, SCO, PO's, ECP, PRR, and VNR; and (2) the system composed of the method of providing home surveillance and care according to the plan of operation described in this document.

Impedance pneumograph. A device (part of the diagnostic bed) that estimates the rate and depth of breathing.

Instrumentation diagnostics kit 130 (IDK). A portable device to quickly test and calibrate the devices in the PSA.

Intensivist. See "Observer".

Lay referral person 136 (LRP). One or more next-of-kin or friends to whom the system refers in event of emergency or other specified events.

Magnetic tape file 100 (Mag-file). Permanent long-term storage of computerized files.

Microfiche file and display 101 (MF&D). This is a photographically reduced record of patient information. It includes medical history and baseline tracings of ECG, BCG, and DUSIAP.

Observer (or "intensivist"). The person who examines incoming patient data in the SCO, refers problems to the appropriate physician, and initiates system responses. This person is well trained in the interpretation of physiologic data, and in the use of all the equipment in the SCO—and preferably also well acquainted with the particular mechanisms by which the PSA collects data, so that the observer can be sensitive to possible causes of artifacts.

Optical glycometer 40 (OG). A device for estimating average blood glucose concentration. It is part of the diagnostic chair.

Ordinary telephone line 70 (for data) (OTLD). These are used to transmit data (via modems) to and from various parts of the system. Though it is not shown in the diagram, these are assumed to be routed through the telephone company switchboard.

Paramedic ready room 128 (PRR). This is a facility where the system's own paramedics are housed while awaiting emergency assignments.

Patient recorder 74 (PR). Part of the PSA, this records all data and communications at the patient's home. This record is not generally available to the patient. It can be accessed by paramedics, nurses, or physicians with a portable terminal.

Patient subscriber (PS). The individual being monitored.

Patient subscriber apparatus 10 (PSA). All devices in the patient's home that monitor his health and report the results to the SCO. These include the BCGwS, BP+GC, DMD, DPPC, modem, and recorder.

Physiologic data display 114 (PDD). This is a video display in the SCO of processed patient data.

Physician's office 118 (PO). The office of the private physician of a particular subscribing patient, equipped with the instrumentation necessary to be a part of the system.

Physicians-on-duty log 98 (PonD-log). A list (in the SCO) of past, present, and predicted times "on duty," the times when a physician signed in or out, and the times a primary physician transferred duty to another physician.

Portable terminal 76 (PT). A device carried by paramedics and nurses (and possibly physicians) in order to access the patient recorder and to communicate data to the SCO.

Private automatic branch exchanger 86 (PABX). The system's private telephone switchboard which handles the switching for all telephonic communications. The system maintains a backup PABX which can be put on-line immediately should the primary PABX fail.

Private dedicated line 721 (PDL). An unshared line from one part of the system to another which is not routed through the telephone company. This can be for either voice or data transmission.

Record-and-display unit 90 (R/D). A device for displaying and recording patient data. The record is a hard copy (written). Both the "pens" and the data are visible during the recording. The record is conveniently visible thereafter.

Surveillance and control office 82 (SCO). The central office for this system. It includes computers for data storage and comparison, displays and records of data, and communication devices to all other parts of the System.

System file 921 (S-file). The hard-copy record of all transmissions between all system elements. This includes records of instrumentation maintenance, installation, calibration, and accounting data.

System progress display 116 (SPD). This is a video display (for the observer) of the current status of emergency measures.

System recorder 91 (SR). This is the apparatus that produces the system-traffic log.

System-traffic log 92 (ST-log). Record of all transmissions to and from the SCO.

Visiting-nurse registry 94 (VNR). A system feature that is optional for each patient subscriber, providing visiting nurses on such schedules as may be negotiated between the patient subscriber and the system management.

5.2 ABBREVIATIONS

BCG—Ballistocardiograph or ballistocardiogram
BCGwS—Ballistocardiograph with sensors
C-file—Computerized file
COC—Computer output comparator
CSS—Computer select switch
CTL—Communications telephone line
DC—Diagnostic chair
DCTL—Dedicated communications telephone line
DDL—Dedicated data line
D-file—Document file
DMD—Daily medicine dispensary
Docu-file—Document file
DPPC—Data preprocessor and converter
DUSIAP—Doppler ultraSonic indirect arterial pressure; the machine for measuring same
ECG—Electrocardiograph or electrocardiogram
ECP—Emergency-call physician
HDC-file—Hard-disk current file
HMSS—Home medical surveillance system
IDK—Instrumentation diagnostic kit
LRP—Lay referral person
Mag-file—Magnetic tape file
MF&D—Microfiche file and display
OG—Optical glycometer
OTLD—Ordinary telephone line (for data)
PABX—Private automatic branch exchanger
PDD—Physiologic data display
PDL—Private dedicated line
PO—Physician's office
PonD-log—Physicians-on-duty log
PR—Patient recorder
PRR—Paramedic ready room
PS—Patient subscriber (i. e., subscribing patient)
PSA—Patient subscriber apparatus
PT—Portable terminal
R/D—Record-and-display unit
SCO—Surveillance and control office
S-file—System file
SPD—System-progress display
SR—System recorder
ST-log—System-traffic recorder log
TL—Telephone line
VNR—Visiting-nurse registry

6. CONCLUSION

The foregoing disclosure is intended to be merely exemplary, not to limit the scope of the invention—which is to be determined by reference to the appended claims.

I claim:

1. A system for medical surveillance and care of spatially distributed, passively-cooperating patients, each of who has a primary physician having a physician's office, by a remote, trained observer, comprising:
   (a) a patient subscriber apparatus located proximate one of said patients operable by the patient without physical interaction with a trained medical personnel including:
      (i) sensing means for automatically sensing, with only passive cooperation by said patient, multiple parameters related to the state of health of said patient constituting in the aggregate a comprehensive profile of said patient's state of health;
      (ii) first electronic means for automatically generating, transmitting and receiving electronic health-parameter signals related to said health parameters;
   (b) at least one surveillance and control office remote from said patient for accommodating said observer, including:
      (i) second electronic means for receiving, generating and transmitting electronic signals to and from said patient subscriber apparatus;
      (ii) display means for selecting and displaying indicia derived from said health-parameter signals;
      (iii) third electronic means for transmitting and receiving data relating to said health parameters of said patient to and from said patient's primary physician's office;
      (iv) means for accommodating such observer, said accommodating means being particularly adapted to afford such observer ready access to the indicia displaying means, and to the second electronic means; and
   (c) fourth electronic means, located in said patient's primary physician's office, for receiving and transmitting data relating to said health parameters of said patient.

2. The apparatus of claim 1, wherein the surveillance and control office further comprises:
   digital-logic computing means for automatically processing at least some of the health-parameter signals received by the second electronic means, and for deriving therefrom indicia signals that represent the health-related parameters for each of such patients; and
   means for applying the indicia signals to control the indicia displaying means.

3. The apparatus of claim 1, wherein:
   the sensing means in each particular patient subscriber apparatus comprise a diagnostic bed that:

is formed to closely accommodate at least portions of the body of the corresponding particular patient, and carries sensors for at least several of the multiple parameters respectively, at specific positions that in use contact respective parts of such patient's body where respective health-parameter phenomena to which the sensors are responsive occur.

4. The apparatus of claim 1, wherein:

the sensing means in each particular patient subscriber apparatus comprise a diagnostic chair that carries sensors for at least two of the multiple parameters respectively, at specific positions that in use adjoin respective parts of such patient's body where respective health-parameter phenomena to which the sensors are responsive occur.

5. The apparatus of claim 1, wherein:

the sensing means in each particular patient subscriber apparatus comprise voice-reception equipment for producing electrical signals related to such patient's speech.

6. The apparatus of claim 1, wherein: the electronic signals that are generated and transmitted by the second electronic means and received by the first electronic means comprise control signals for controlling the sensing means in the patient subscriber apparatus.

7. The apparatus of claim 1, wherein:

each patient subscriber apparatus further comprises a daily medicine dispensary that:

receives and contains packaged medications for a multiplicity of days at one time;

automatically meters out the particular allotments of medication for such partaicular patient;

automatically monitors withdrawal of the medication allotments, and transmits to the surveillance and control office information derived from the automatic monitoring.

8. The apparatus of claim 1, wherein:

each patient subscriber apparatus further comprises means for recording the health-parameter signals;

the surveillance and control office further comprises means for recording the signals received by the second electronic means; and the system further comprises a portable terminal retrieving and displaying the recorded health-parameter signals from the patient subscriber apparatus, whereby the health-parameter signals are received and recorded in the surveillance and control office and are accessible by means of the portable terminal to personnel in such patient's home.

9. The apparatus of claim 1, wherein:

(a) the sensing means in each particular patient subscriber apparatus comprises:

(i) a diagnostic bed that is formed to closely accommodate at least portions of the body of the corresponding particular patient, and that carries sensors for at least several of the multiple parameters respectively, at specific positions that in use contact respective parts of such patient's body where respective healthparameter phenomena to which the sensors are responsive occur;

(ii) a diagnostic chair that carries sensors for at least two of the multiple parameters respectively, at specific positions that in use adjoin respective parts of such patient's body where respective healthparameter phenomena to which the sensors are responsive occur;

(iii) voice-reception equipment for producing electrical signals related to such patient's speech;

(b) the electronic signals that are generated and transmitted by the second electronic means and received by the first electronic means comprise control signals for controlling the sensing means in the patient subscriber apparatus; and (c) each patient subscriber apparatus further comprises a daily medicine dispensary that:

(i) receives and contains packaged medications for a multiplicity of days at one time, (ii) automatically meters out the particular allotments of medication for such particular patient, (iii) automatically monitors withdrawal of the medication allotments, and (iv) transmits to the surveillance and control office information derived from the automatic monitoring.

10. The system of claim 1, further comprising an emergency-call physician's office including:

fifth electronic means for transmitting and receiving data relating to said health parameters of said patient to and from said surveillance and control office;

means for communicating with said surveillance and control office and said observer; and means for communicating with a paramedic ready-room.

11. The system of claim 1, further comprising a paramedic ready-room including:

sixth electronic means for transmitting and receiving data relating to said health parameters of said patient to and from said surveillance and control office;

means for communicating with said surveillance and control office and said observer;

means for communicating with an emergency-call physician's office; and means for communicating with said patient's primary physician's office.

12. A method of providing home medical surveillance and care of patients, each of who has a primary physician having an office, by a remote, trained observer, comprising the steps of:

routinely obtaining a multiplicity of measurements related to the state of health of each such patient by remote automatic sensing equipment which is operable by the patient without physical interaction with a trained medical personnel while such patient is at home, with no more than passive cooperation by such patient, wherein passive cooperation comprises each such patient moving to and emplacing himself/herself upon the means for automatically sensing;

receiving the results of all of such routine measurements by remote data transmission into a central office, and displaying the results in the central office for routine review by such observer;

transmitting and receiving data relating to said measurement results to and from said patient's primary physician's office;

in emergencies for any particular such patient, obtaining a multiplicity of measurements related to the state of health of that patient while such patient is at home, with no more than passive cooperation by such patient;

receiving the results of all such emergency measurements by remote data transmission into a central office, and displaying the results of such emergency measurements for emergency review by such observer;

said observer determining the general state of health of such patient from such routine and emergency measurements;

said observer determining from the general state of health of such patient whether a nonroutine therapeutic response should be provided; and if so, said observer facilitating such a nonroutine therapeutic response.

13. The method of claim 12, wherein:

the measurement-obtaining steps comprise the patient's reclining in a diagnostic bed that:

is formed to closely accommodate at least portions of the body of the particular patient, and carries sensors for at least several of the multiplicity of measurements respectively, at specific positions that in use contact respective parts of such patient's body where respective health-related phenomena to which the sensors are responsive occur.

14. The method of claim 12, wherein:

the measurement-obtaining steps comprise the patient's sitting in a diagnostic chair that carries sensors for at least two of the multiplicity of measurements respectively, at specific positions that in use adjoin respective parts of such patient's body where respective health-parameter phenomena to which the sensors are responsive occur.

15. The method of claim 12, further comprising the step of:

automatically metering out periodic allotments of medication for such patient; and monitoring withdrawal of the allotments by such patient.

16. The method of claim 12, further comprising the steps of:

notifying such patient's regular physician in event of any emergency; and also providing immediate medical response in event of any extreme emergency.

17. The method of claim 12, wherein the steps of facilitating a nonroutine therapeutic response further comprises:

transmitting and receiving data relating to said results of said emergency measurements to and from an emergency-call physician in an emergency-call physician's office.

18. The method of claim 12, wherein the step of facilitating a nonroutine therapeutic response further comprises:

transmitting and receiving data relating to said results of said emergency measurements to and from a paramedic in a paramedic-ready room.

* * * * *